US012778504B2

(12) United States Patent
Everman et al.

(10) Patent No.: US 12,778,504 B2
(45) Date of Patent: Nov. 3, 2026

(54) WEARABLE HEADGEAR AND METHODS FOR MANUFACTURING WEARABLE HEADGEAR

(71) Applicant: GMECI, LLC, Beavercreek, OH (US)

(72) Inventors: Bradford R. Everman, Haddonfield, NJ (US); Brian Scott Bradke, Brookfield, VT (US)

( * ) Notice: Subject to any disclaimer, the term of this patent is extended or adjusted under 35 U.S.C. 154(b) by 0 days.

(21) Appl. No.: 18/775,691

(22) Filed: Jul. 17, 2024

(65) Prior Publication Data

US 2026/0020820 A1 Jan. 22, 2026

(51) Int. Cl.

*A61B 5/00* (2006.01)
*A61B 5/1455* (2006.01)
*A61B 5/375* (2021.01)
*G06N 20/00* (2019.01)

(52) U.S. Cl.

CPC ........ *A61B 5/6803* (2013.01); *A61B 5/14551* (2013.01); *A61B 5/375* (2021.01); *A61B 5/7207* (2013.01); *A61B 5/7267* (2013.01); *G06N 20/00* (2019.01)

(58) Field of Classification Search

CPC .............. A61B 5/6803; A61B 5/14551; A61B 5/375; A61B 5/7207; A61B 5/7267

See application file for complete search history.

(56) References Cited

U.S. PATENT DOCUMENTS

| | | | | |
|---|---|---|---|---|
| 11,461,991 | B2 | 10/2022 | Troisi | |
| 11,478,184 | B1 | 10/2022 | Dagum | |
| 2019/0167211 | A1* | 6/2019 | Everman | G09B 9/10 |
| 2020/0373001 | A1* | 11/2020 | Harrison | G06Q 30/0631 |
| 2023/0309860 | A1 | 10/2023 | Komeilipoor | |

* cited by examiner

*Primary Examiner* — Tammie K Marlen
(74) *Attorney, Agent, or Firm* — CALDWELL LLC

(57) ABSTRACT

A wearable headgear including at least a sensor positioned within the wearable headgear, wherein the at least a sensor includes at least an electroencephalographic sensor and at least a circulatory sensor, a signal processing module communicatively connected to the at least an electroencephalographic sensor, and a system including a processor, a memory communicatively connected to the a processor, the memory configuring the processor to detect a reaction as a function of the at least a sensor, generate sensor output signals as a function of the reaction, generate an action response as a function of the sensor output signals and activate an operation circuit as a function of the action response.

9 Claims, 12 Drawing Sheets

300

WEARABLE HEADGEAR AND METHODS FOR MANUFACTURING WEARABLE HEADGEAR

FIELD OF THE INVENTION

The present invention generally relates to the field of sensors within wearable headgear. In particular, the present invention is directed to an apparatus and method for manufacturing wearable headgear.

BACKGROUND

Wearable headgear, designed for operators of moving vehicles, is essential for continuously monitoring a range of vital operator conditions during movement, thereby playing a critical role in upholding and enhancing vehicular safety. However, the existing technological framework, particularly in the context of vehicle operators, is limited by current use of EEG sensors alone.

SUMMARY OF THE DISCLOSURE

In an aspect, wearable headgear comprising at least a sensor positioned within the wearable headgear, wherein the at least a sensor further comprises: at least an electroencephalographic sensor; and at least a circulatory sensor configured; a signal processing module communicatively connected to the at least an electroencephalographic sensor, wherein the signal processing module is configured to filter motion artifacts from the electroencephalographic sensor. The system including at least a processor; a memory communicatively connected to the at least a processor, the memory containing instructions configuring the processor to: detect a reaction as a function of the at least a sensor; generate sensor output signals as a function of a detected reaction; receive a plurality of sensor outputs from the sensor; generate an action response as a function of the plurality of sensor output signals; and activate an operation circuit as a function of the action response.

In another aspect, a method for manufacturing a wearable headgear including filtering, by a signal processing module, motion artifacts from an electroencephalographic sensor; detecting a reaction as a function of the at least a sensor; generating sensor outputs as a function of a detected reaction; receiving a plurality of sensor output signals from the sensor; generate an action response as a function of the plurality of sensor outputs; and activating an operation circuit as a function of the action response.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for an apparatus for wearable headgear. In an embodiment, the wearable headgear comprises at least a sensor positioned within the headgear apparatus.

Aspects of the present disclosure can be used to utilize eye tracking to activate response devices. Aspects of the present disclosure can also be used to determine a cognitive state of a user. This is so, at least in part, because the apparatus detects reactions of the user.

Figure 1:
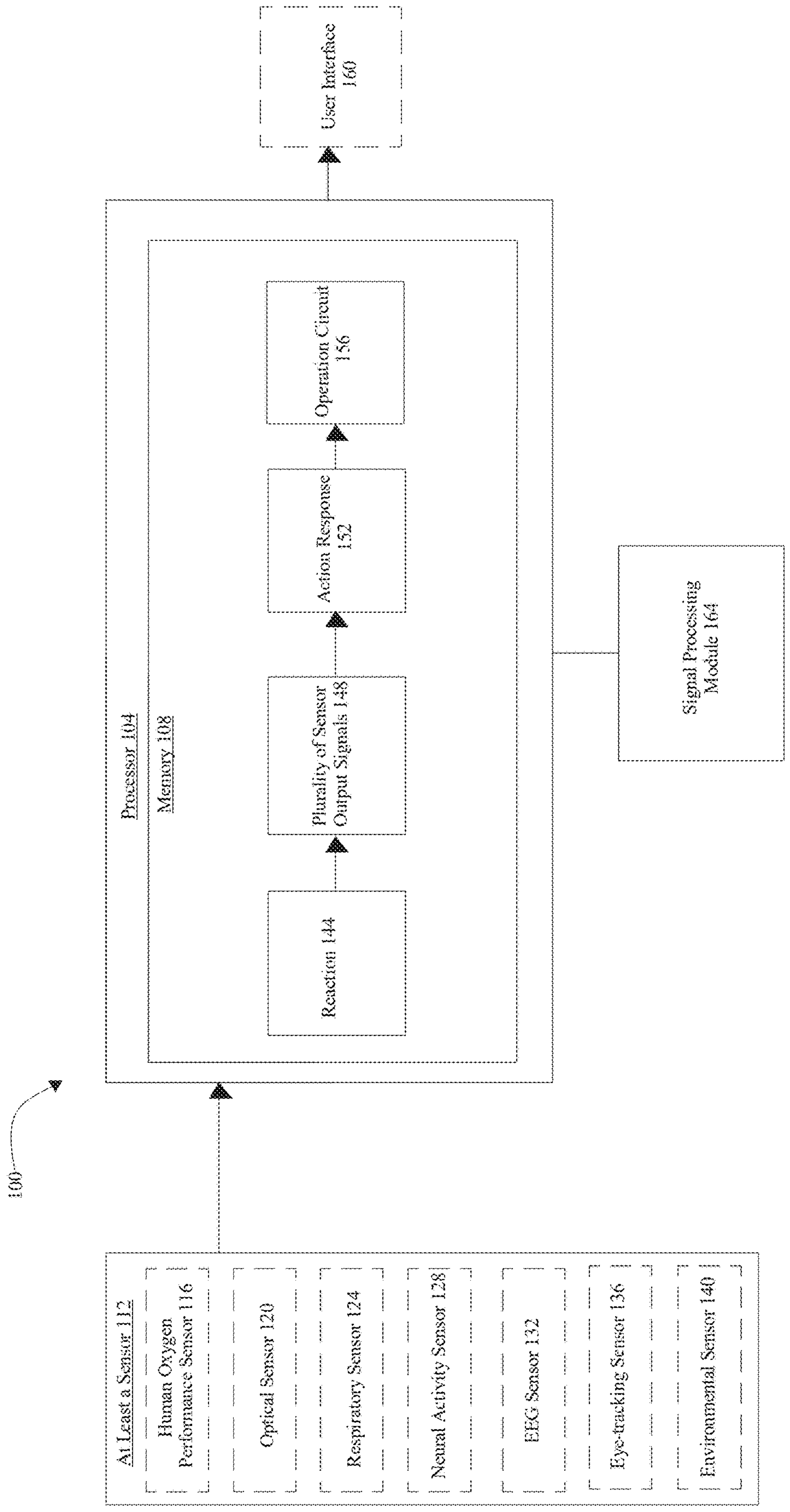
FIG. 1 is a block diagram illustrating an exemplary system for wearable headgear.

Referring now to FIG. 1, an exemplary embodiment for wearable headgear is illustrated. Headgear 100 includes a processor 104. Headgear includes a processor communicatively connected to a memory 108. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

With reference to FIG. 1, headgear 100 may include a standalone wearable headgear. Standalone wearable headgear may include a plurality of housings. As used in the current disclosure, a "housing" is a rigid casing that encloses equipment. Housing may be constructed of any material or combination of materials, including without limitation metals, polymer materials such as plastics, wood, fiberglass, carbon fiber, or the like. In an embodiment, housing is shaped to conform to a particular portion of user anatomy when placed on exterior body surface. In a non-limiting embodiment, wearable headgear may feature a headband, headphones, or analogous device. In another non-limiting embodiment, wearable headgear may feature a ring encircling the ear, leaving it exposed. The wearable headgear may be reminiscent of a bike helmet or headphone design without the enclosing element. When placed to so conform, housing may position at least a sensor and/or user signaling device in a locus chosen as described in further detail below. For example, at least a sensor 112 may be mounted within housing, such that the at least a sensor 112 is placed in contact with a user's skin during use. For instance, where housing is incorporated in a helmet, mask, earcup or headgear, housing may be positioned at a particular portion of user's head when helmet, mask, earcup or headset is worn, which may in turn position at least a sensor and/or user signaling device at a particular locus on user's head or neck. Headgear 100 and housing are discussed in further with respect to FIG. 2A-C.

Still referring to FIG. 1, processor 104 may be configured to be wirelessly connected to a user device. As used in the current disclosure, a "user device" is an electronic device such as a computing device, smartphone, tablet, laptop, smart watch, fitness tracker, FITBIT, wearable, and the like. In an embodiment at least a sensor may be located on or communicative by way of a user device. User device may be connected to processor 104 using internet, Wi-Fi, Bluetooth, cellular communication, radio communication, satellite communication, and the like. As used in the current disclosure, "Bluetooth" is a short-range wireless technology standard that is used for exchanging data between fixed and mobile devices over short distances. In embodiments, Bluetooth may use UHF radio waves in the ISM bands, from 2.402 GHz to 2.48 GHz, and building personal area networks (PANs). Bluetooth may be used to exchange files between nearby user devices. Bluetooth may be used to connect user devices with wearable headgear.

With reference to FIG. 1, Headgear 100 may include at least a sensor 112 positioned within the headgear apparatus. As used in this disclosure, "at least a sensor" is configured to detect at least a cognitive parameter and transmit an electrical signal as a result of the detected parameter. The proper placement of at least one sensor within the headgear apparatus is paramount to its optimal functionality. Processor 104 can utilize a software protocol designed to aid users in positioning the sensor accurately. This protocol may employ various cues such as alerts and voice notifications, guiding users towards the optimal placement. The software protocol may operate by utilizing a signal to noise ratio as an input parameter and then direct the user to move the sensor such that it minimizes signal to noise. Signal to noise ratio may be calculated, as a non-limiting example, be calculated by dividing signal power by noise power. For example, if a user moves the sensor and the signal to noise ratio increases, then that would mean that the user is moving the sensor in the correction direction. In some embodiments, the software may determine a direction of greatest decrease in signal to noise ratio and coach the user to move the sensor in that direction. The software protocol may also use motion artifact determination functions to detect motion artifacts and then direct placement to minimize them. Voice prompts may provide directional guidance, instructing users to adjust the sensor position accordingly, for instance, by indicating movements such as "to the right," "to the left," "up," "down," and the like. As used herein, a "cognitive parameter" refers to the mental or emotional state of the user. Examples of cognitive parameters may include measurements of the alertness, nervousness, apprehensiveness, and the like of the user. At least a sensor may be used to detect at least a physiological parameter of the user. As used herein, transmission of an electrical signal may include any detectable alternation of an electrical parameter of an electrical circuit. As used herein, "at least a physiological parameter" refers to any datum that may be captured by a sensor and describes the physiological state of the user. For instance, at least a sensor 112 may increase or reduce the impedance and/or resistance of a circuit to which at least a sensor 112 is connected. At least a sensor 112 may alter a voltage or current level, frequency, waveform, amplitude, or other characteristic at a locus in circuit. Transmission of an electrical signal may include modulation or alteration of power circulating in circuit; for instance transmission may include closing a circuit, transmitting a voltage pulse through circuit, or the like. Transmission may include driving a non-electric signaling apparatus such as a device for transmitting a signal using magnetic or electric fields, electromagnetic radiation, optical or infrared signals, or the like. At least a sensor may be placed in locations suitable for detection of neural activity, such as on upper surfaces of a cranium of the user, or similar locations that are suitable for EEG or MEG detection and measurement.

Continuing reference to FIG. 1, detection of at least a physiological parameter, as used herein, includes detection of any datum describing a physiological state of user. At least a sensor may include at least a circulatory sensor, defined for the purposes of this specification as a sensor configured to detect at least a circulatory parameter. At least a physiological parameter may include at least a circulatory parameter, which may include any detectable parameter describing the state of blood vessels such as arteries, veins, or capillaries, any datum describing the rate, volume, pressure, pulse rate, or other state of flow of blood or other fluid through such blood vessels, chemical state of such blood or other fluid, or any other parameter relative to health or current physiological state of user as it pertains to the cardiovascular system. As a non-limiting example, at least a circulatory parameter may include a blood oxygenation level of user's blood. At least a circulatory parameter may include a pulse rate. At least a circulatory parameter may include a blood pressure level. At least a circulatory parameter may include heart rate variability and rhythm. At least a circulatory parameter may include a plethysmograph describing user blood-flow; in an embodiment, plethysmograph may describe a reflectance of red or near-infrared light from blood. One circulatory parameter may be used to determine, detect, or generate another circulatory parameter; for instance, a plethysmograph may be used to determine pulse oxygen level (for instance by detecting plethysmograph amplitude), pulse rate (for instance by detecting plethysmograph frequency), heart rate variability and rhythm (for instance by tracking pulse rate and other factors over time), and blood pressure, among other things. In a non-limiting embodiment, at least a physiological parameter may include neural oscillations generated by user neurons, including without limitation neural oscillations detected in the user's cranial region, sometimes referred to as "brainwaves." Neural oscillations include electrical or magnetic oscillations generated by neurological activity, generally of a plurality of neurons, including superficial cranial neurons, thalamic pacemaker cells, or the like. Neural oscillations may include alpha waves or Berger's waves, characterized by frequencies on the order of 7.5-12.5 Hertz, beta waves, characterized by frequencies on the order of 13-30 Hertz, delta waves, having frequencies ranging from 1-4 Hertz, theta waves, having frequencies ranging from 4-8 Hertz, low gamma waves having frequencies from 30-70 Hertz, and high gamma waves, which have frequencies from 70-150 Hertz. Neurological oscillations may be associated with degrees of wakefulness, consciousness, or other neurological states of user, for instance as described in further detail below.

Continuing reference to FIG. 1, at least a sensor 112 may comprise a human oxygen performance sensor 116. As used in this disclose, a "human performance oxygen sensor" refers to a sensor that measures an individual human being's vital oxygenation signals. Human performance oxygen sensor 116 may measure pulse oximetry, pule, temperature, and the like. In a non-limiting embodiment, the human performance oxygen sensor may store data gathered from detected measurements within a storage medium housed within the human oxygen performance sensor 116. In a non-limiting embodiment, human performance oxygen sensor may transmit the detected measurements to one or more remote storage mediums through one or more wired and/or wireless means. In an embodiment, the human performance oxygen sensor may compare data gathered from detected measurements to a table of known human performance. In a non-limiting embodiment, the human performance oxygen sensor may include a printed circuit board housed within an outer shell. According to an embodiment, the printed circuit board may include a battery or other power supply, one or more recording devices, one or more accelerometers, one or more processors (configured to perform one or more of the tasks of the printed circuit board), and/or any other suitable components, while maintaining the spirit of the present invention. According to an embodiment, the one or more processors may be a component of the printed circuit board. Additional disclosure related to human oxygen performance sensors is included in U.S. patent application Ser. No. 15/492,612 entitled "HUMAN PERFORMANCE OXYGEN SENSOR," by B. Everman et al., which is incorporated herein by reference in its entirety.

Continuing reference to FIG. 1, at least a sensor 112 may include an optical sensor 120, which detects light emitted, reflected, or passing through human tissue. Optical sensor may include a near-infrared spectroscopy sensor (NIRS). A NIRS, as used herein, is a sensor that detects signals in the near-infrared electromagnetic spectrum region, having wavelengths between 780 nanometers and 2,500 nanometers. NIRS sensors are discussed in further detail with reference to FIG. 4.

With continued reference to FIG. 1, at least a sensor 112 may include at least a respiratory sensor 124. As used in this disclosure, a "respiratory sensor" is a sensor configured to detect a respiration parameter representative of a phenomenon associated with respiration, for example without limitation respiration of a user. Respiratory sensor may be configured to detect a respiration parameter associated with a user. Respiration sensor may include any sensor described in this disclosure, including without limitation a blood oxygen meter. As used in this disclosure, a "respiration parameter" is at least an element of data representative of a phenomenon associated with respiration, for example without limitation respiration of a user. In some embodiments, at least a respiratory sensor may include at least an inhalation sensor. As used in this disclosure, an "inhalation sensor" is a sensor configured to detect an inhalation parameter representative of a phenomenon associated with inhalation, for example without limitation inhalation of a user. Inhalation sensor may include any inhalation sensor described in this disclosure. In some cases, inhalation sensor may include an inspirate sensor. In some embodiments, at least a respiratory sensor may include at least an exhalation sensor. As used in this disclosure, a "exhalation sensor" is a sensor configured to detect an exhalation parameter representative of a phenomenon associated with exhalation, for example without limitation exhalation of a user. An exemplary non-limiting respiration parameter includes blood oxygen level SpO2.

Continuing reference to FIG. 1, at least a sensor 112 may include a neural activity sensor 128. A neural activity sensor, as used herein, includes any sensor disposed to detect electrical or magnetic phenomena generated by neurons, including cranial neurons such as those located in the brain or brainstem. Neural activity sensor 128 may include an electroencephalographic sensor. Neural activity sensor may include a magnetoencephalographic sensor. In an embodiment, neural activity sensor may be configured to detect neural oscillations.

Continuing reference to FIG. 1, at least a sensor 112 may be configured to measure electroencephalography brain wave data (EEG) using an EEG sensor 132. As used in this disclosure, an "EEG sensor" is a sensor that is configured to detect an EEG parameter representative of a phenomenon associated with EEG sensing, such as electrical activity in the cerebral cortex, Beta Waves associated with alert states, Alpha Waves associated with relaxed states, theta waves associated with drowsiness states and the like. EEG sensors operate based on the principle that brain cells (neurons) communicate with each other through electrical impulses. When neurons are active, they can produce electrical patterns that can be detected and measured using at least a sensor 112. Raw EEG signals can be identified as distinct waves with different frequencies. EEG sensor 132 may be configured to read Beta Waves (frequency range from 14 Hz to 30 Hz). Beta waves may be associated with being conscious or in an awake, attentive, alert state. Low-amplitude beta waves may be associated with active concentration, or with a busy or anxious state of mind. Beta waves may also be associated with motor decisions such as suppression of movement and sensory feedback of motion. EEG sensor 132 may be configured to read Alpha Waves (frequency range from 7 Hz to 13 Hz). Alpha Waves may be associated with a relaxed, calm and lucid state of mind. Alpha waves can be found in the occipital and posterior regions of the brain. EEG sensor 132 may be configured to read Theta Waves (frequency range from 4 Hz to 7 Hz). Theta waves may be used to measure drowsiness. In a non-limiting embodiment, EEG may involve placing electrodes on the scalp. In a non-limiting embodiment, EEG may be integrated within an earpiece in wearable headgear. EEG sensors may be used to measure at least a cognitive parameter of the user.

Continuing reference to FIG. 1, at least a sensor 112 may include an eye-tracking sensor, such as one or more cameras for tracking the eyes of user. Eye-tracking sensor may include, as a non-limiting example, one or more electromyographic sensors, which may detect electrical activity of eye muscles; electrical activity may indicate activation of one or more eye muscles to move the eye and used by a circuit such as an alert circuit as described below to determine a movement of user's eyeball, and thus its current location of focus.

Continuing reference to FIG. 1, at least a sensor 112 may include at least an environmental sensor 140. As used herein, at least an environmental sensor may be any sensor configured to detect at least an environmental parameter, defined herein as a parameter describing non-physiological data concerning user or surroundings of user, such as acceleration, carbon monoxide, or the like. At least an environmental sensor may include at least a motion sensor, including without limitation one or more accelerometers, gyroscopes, magnetometers, or the like; at least a motion sensor may include an inertial measurement unit (IMU). At least an environmental sensor may include at least a temperature sensor. At least an environmental sensor may include at least an air quality sensor, such as without limitation a carbon monoxide sensor. At least an environmental sensor may include a pressure sensor, for instance to detect air or water pressure external to user.

With continued reference to FIG. 1, processor 104 may be configured to detect a reaction 144 as a function of the at least a sensor 112. As used herein, a "detected reaction" refers to at least a change in the condition of the user. In a non-limiting embodiment, a detected reaction may include a detection of a cognitive or physiological alarm condition. In a non-limiting embodiment, a cognitive alarm datum includes any cognitive condition of a user that may endanger user or impair user's ability to perform an important task. In a non-limiting example, if a user is flying an aircraft and the user's cognitive condition is such that the user is extremely anxious, to the point where they may have blurred judgement, a cognitive alarm may exist. In non-limiting embodiment, a physiological alarm condition includes any physiological condition of user that may endanger user or impair user's ability to perform an important task; as a non-limiting example, if user is flying an aircraft and user's physiological condition is such that user is unable to concentrate, respond rapidly to changing conditions, see or otherwise sense flight controls or conditions, or otherwise successfully operate the aircraft within some desired tolerance of ideal operation, a physiological alarm condition may exist, owing to the possibility of inefficient or dangerous flight that may result. Similarly, if user's physiological condition indicates user is experiencing or about to experience physical harm, is losing or is about to lose consciousness, or the like, a physiological alarm condition may exist.

Continuing reference to FIG. 1, detection of reaction 144 may include comparison of at least a cognitive or physiological parameter to a threshold level. In a non-limiting example, detection of the cognitive alarm condition comprises determination that the at least a cognitive parameter is falling below a threshold level; as an example, anxiety levels above a certain cutoff indicate an imminent anxiety attack. For instance, and without limitation, detection of the physiological alarm condition further comprises determination that the at least a physiological parameter is falling below a threshold level; as an example, blood oxygen levels below a certain cutoff indicate an imminent loss of consciousness, as may blood pressure below a certain threshold. Similarly, alpha wave activity falling below a certain point may indicate entry into early stages of sleep or a hypnogogic state. Comparison to threshold may include comparison of at least a physical parameter to a value stored in memory, which may be a digitally stored value; alternatively or additionally comparison may be performed by analog circuitry, for instance by comparing a voltage level representing at least a physical parameter to a reference voltage representing the threshold, by means of a comparator or the like. Threshold may represent or be represented by a baseline value. Detection of a reaction condition may include comparing at least a cognitive or physiological parameter to at least a baseline value and detecting the reaction as a function of the comparison. At least a baseline value may include a number or set of numbers representing normal or optimal function of user, a number or set of numbers representing abnormal or suboptimal function of user, and/or a number or set of numbers indicating one or more cognitive or physiological parameters demonstrating a reaction, such as a physical alarm condition. At least a baseline value may include at least a threshold as described above. In an embodiment, at least a baseline value may include a typical user value for one or more physiological parameters. For example, and without limitation, at least a baseline value may include a anxiety level, alertness level, blood oxygen level, blood pressure level, pulse rate, or other circulatory parameter, or range thereof, consistent with normal or alert function in a typical user; at least a baseline value may alternatively or additionally include one or more such values or ranges consistent with loss of consciousness or impending loss of consciousness in a typical user. Similarly, at least a baseline value may include a range of neural oscillations typically associated in users with wakeful or alert states of consciousness, and/or a range of neural oscillations typically associated with sleeping or near-sleeping states, loss of consciousness or the like. Additional disclosure related to physical alarm conditions is included in U.S. patent application Ser. No. 16/012,713 entitled "SYSTEMS AND METHODS FOR MEASURING PHYSIOLOGICAL PARAMETERS," by B. Everman et al., which is incorporated herein by reference in its entirety.

With continued reference to FIG. 1, detection of reaction 144 may further include detection of at least an environmental parameter, and detection of a reaction as a function of the at least an environmental parameter. For instance, aggregation of detected reactions may determine that a reduction in cranial blood pressure coupled with an increase in acceleration indicates a probable loss of consciousness in a user; an alarm may therefore be triggered by detection, by the at least a sensor 112, of that combination of decreased cranial blood pressure and increased acceleration.

Continuing reference to FIG. 1, in a non-limiting embodiment, detection of reaction 144 may include a determination, by the at least a sensor 112, that a user is losing consciousness. Alternatively or additionally, detection may include determination that user is about to lose consciousness. This may be achieved by comparing one or more cognitive or physiological parameters and/or environmental parameters to a relationship, threshold, or baseline, which may be any relationship, threshold, or baseline as described above; for instance and without limitation, where blood oxygen level drops below a threshold percentage of a baseline level, below an absolute threshold amount, below a certain number of standard deviations, or the like, at least a sensor 112 may determine that user is about to lose consciousness or is losing consciousness, and issue an alarm. Alternatively or additionally, an aggregation of detected reactions may determine that imminent loss of consciousness is predicted by a particular set of values for one or more parameters as described above, at least a sensor 112 may detect a reaction by detecting the particular set of values, indicating that user is about to lose consciousness.

With continued reference to FIG. 1, processor 104 may be configured to generate a plurality of sensor output signals 148 as a function of the detected reaction 144. As used in this disclosure, a "sensor signal" is a representation of a sensed information that at least a sensor 112 may generate. A sensor signal may include any signal form described in this disclosure, for example digital, analog, optical, electrical, fluidic, and the like. In some cases, a sensor, a circuit, and/or a controller may perform one or more signal processing steps on a signal. For instance, sensor, circuit, and/or controller may analyze, modify, and/or synthesize a signal in order to improve the signal, for instance by improving transmission, storage efficiency, or signal to noise ratio. Sensor output signals 148 may output to a control circuit.

With continued reference to FIG. 1, processor 104 may be configured to generate an action response 152 as a function of the plurality of sensor output signals 148. As used herein, an "action response" refers to a feedback response that is a result of the plurality of sensor output signals. An action response may take the form of a signal. As used in this disclosure, a "signal" is any intelligible representation of data, for example from one device to another. A signal may include an optical signal, a hydraulic signal, a pneumatic signal, a mechanical, signal, an electric signal, a digital signal, an analog signal and the like. In some cases, a signal may be used to communicate with a computing device, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

With continued reference to FIG. 1, headgear may include a signal processing module 164. As used herein, a "signal processing module" refers to a component that is designed to manipulate or analyze signals. Signal processing module 164 may analyze, modify, and/or synthesize a signal representative of the action response 152 in order to improve the signal, for instance by improving transmission, storage efficiency, or signal to noise ratio. Signal processing module 164 may include analog circuitry, digital circuitry (including combinatorial and sequential logic), and the circuitry could be FPGA, ASIC, could include ROM for coefficients, including rewritable ROM, or other memory such as flash memory that is loaded to registers on bootup. Signal processing module 164 may also be adaptive, for example, trained with "ideal" and "noisy" signals to cancel or filter out noise, effects of motion, etc. In an embodiment, adaptive filters may include Weiner, Kalman, least-squares, least mean squares, Frequency Domain Adaptive Filters (FDAF), or the like. Signal Processing module 164 may include a software module, a system on a chip with processor 104 or another processor, and/or entirely in processor 104 as a purely software filter. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which varying continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 1, signal processing module 164 may be communicatively connected to the at least an electroencephalographic sensor. Signal processing module 164 may be configured to filter motion artifacts from the electroencephalographic sensor. As used herein, "motion artifacts" refer to noise or other distortions/effects on signals. In a non-limiting embodiment, motion artifacts may occur by being mounted on a user's head, moving relative to the head, getting muscular electrical signals, being in an aircraft, etc.

With continued reference to FIG. 1, action response 152 may utilize a filtration process when analyzing at least an EEG sensor. As used herein, a filtration process" refers to a process of filtering unwanted signals and sensed motion artifacts. In a non-limiting embodiment, the filtration process may comprise motion artifact rejection filtering. Motion artifact rejection filtering may remove or minimize the effects of motion artifacts, which may include unwanted alterations in senses signals caused by movement. For example, when a user is wearing the wearable headgear while in flight, the at least electrodes located within the wearable headgear may shift, creating changes in the electrical signals that are not related to the physiological phenomenon being measured. In non-limiting embodiments, motion artifact rejection filtering may utilize digital signal processing (DSP) filters. DSP filters may be adaptive or fixed. Adaptive filters may adjust their parameters in real-time based on characteristics of incoming EEG signals, while fixed filters use a constant set of parameters. In another non-limiting embodiment, motion artifact rejection filtering may utilize time-domain analysis, which may involve inspecting the signal over time to identify and remove segment that are likely to be contaminated with motion artifacts. The motion artifact rejection filtering may use frequency-domain analysis, wavelet transform, independent component analysis, and the like.

With continued reference to FIG. 1, generating action response 152 may include an action response machine learning model. An action response machine learning model may be trained with action response training data correlating the plurality of sensor outputs to action responses. Action response training data may be received from user input, external computing devices, and/or iterations of processing. Action response machine learning model may input plurality of sensor outputs and output action responses. Action response machine learning model may be consistent with the machine learning models described below in FIG. 5. Inputs to the action response machine learning model may include a plurality of sensor outputs, detected reactions, user data, historical versions of action responses, examples of action responses, and the like. Outputs to the action response machine learning model may include an action response. Action response training data may include a plurality of data entries containing a plurality of inputs that are correlated to a plurality of outputs for training a processor by a machine-learning process. Outputs to the machine-learning process may be used as inputs for an updated machine-learning process. In an embodiment, action response training data may be iteratively updated as a function of the input and output results of past action response machine learning models or any other machine learning model mentioned throughout this disclosure. The machine learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, headgear 100 may include at least a user interface 160. As used in this disclosure, a "user interface" is a system that is designed and/or configured to facilitate communication between at least a system, such as without limitation a processor, and a user by way of at least an output communicated to the user and/or at least an input communicated from the user. Exemplary non-limiting user interfaces 160 include displays, audio systems, haptic systems, head mounted displays, mice, joysticks, keyboards, and the like. User interface 160 may be configured to alert the user as a function of the imminent loss of consciousness event. In some cases, user interface 160 may include headphones, for example over ear headphones including an earcup. In some cases, user interface may include a bone conducting transducer, for example located within an earcup of a headphone. A "bone-conducting transducer," as used in this disclosure, is a device or component that converts an electric signal to a vibrational signal that travels through bone in contact with the device or component to an inner ear of user, which interprets the vibration as an audible signal. Bone-conducting transducer may include, for instance, a piezoelectric element, which may be similar to the piezoelectric element found in speakers or headphones, which converts an electric signal into vibrations. In an embodiment, bone-conducting transducer may be mounted to housing in a position placing it in contact with a user's bone; for instance, where housing includes or is incorporated in an ear cup, housing may place bone-conducting transducer in contact with user's skull just behind the ear, over the sternocleidomastoid muscle. Likewise, where housing includes a headset, mask, or helmet, housing may place bone-conducting transducer in contact with a portion of user's skull that is adjacent to or covered by headset, mask, or helmet. Additional disclosure related to headphones and bone conducting transducers may be found in U.S. patent application Ser. No. 16/859,483 filed on Apr. 27, 2020, entitled "HUMAN PERFORMANCE OXYGEN SENSOR," the entirety of which is incorporated herein by reference.

Still referring to FIG. 1, in some embodiments, at least a user interface 160 may include an audio system. As used in this disclosure, an "audio system" is a system that is configured to transduce a signal to sound and/or vice versa. Non-limiting exemplary audio systems include loudspeakers, headphones, microphones, bone-conducting transducers, and the like. In some cases, at least a user interface may be configured to generate auditory coaching to user, for instance as a function of imminent loss of consciousness event. As used in this disclosure, "auditory coaching" is audio instructions intended for a user to listen and respond to. Auditory coaching may be selected based upon condition. For example, different auditory coaching may be selected for G-induced loss of consciousness, hypocapnia, hypoxia, and the like. Auditory coaching may include any instructions to avoid an imminent loss of consciousness event described in this disclosure, including those described in detail below.

Still referring to FIG. 1, processor 104 may be configured to activate an operation circuit 156 as a function of the action response 152. As used herein an "operation circuit" refers to specialized signal configuration designed to initiate a specific process in response to a detected action or stimulus. Operation circuit 156 may transmit at least a signal to control or alter at least an interaction with the user, control of a muti-functional display, pilot controls, and the like as a function of the action response. In a non-limiting example, operation circuit may be configured to interact with one or more pilot controls of an aircraft including, without limitation, turning, braking. liftoff, landing, climbing, cruising and the like. In a non-limiting embodiment, activating the operation circuit as a function of the action response may allow the user to use optical sensors and eye-tracking to shift views of a multi-functional display. In another embodiment, an action response indicating that a user has an extremely high anxiety level may initiate an operation circuit to signal to external communication lines that the user may not be able to make intelligent or normal decisions while operating an aircraft. In another embodiment, an action response indicating that the user's blood oxygen levels are very low may initiate an operation circuit to signal to the user an alert that their blood oxygen levels are dangerously low.

Figure 2A:
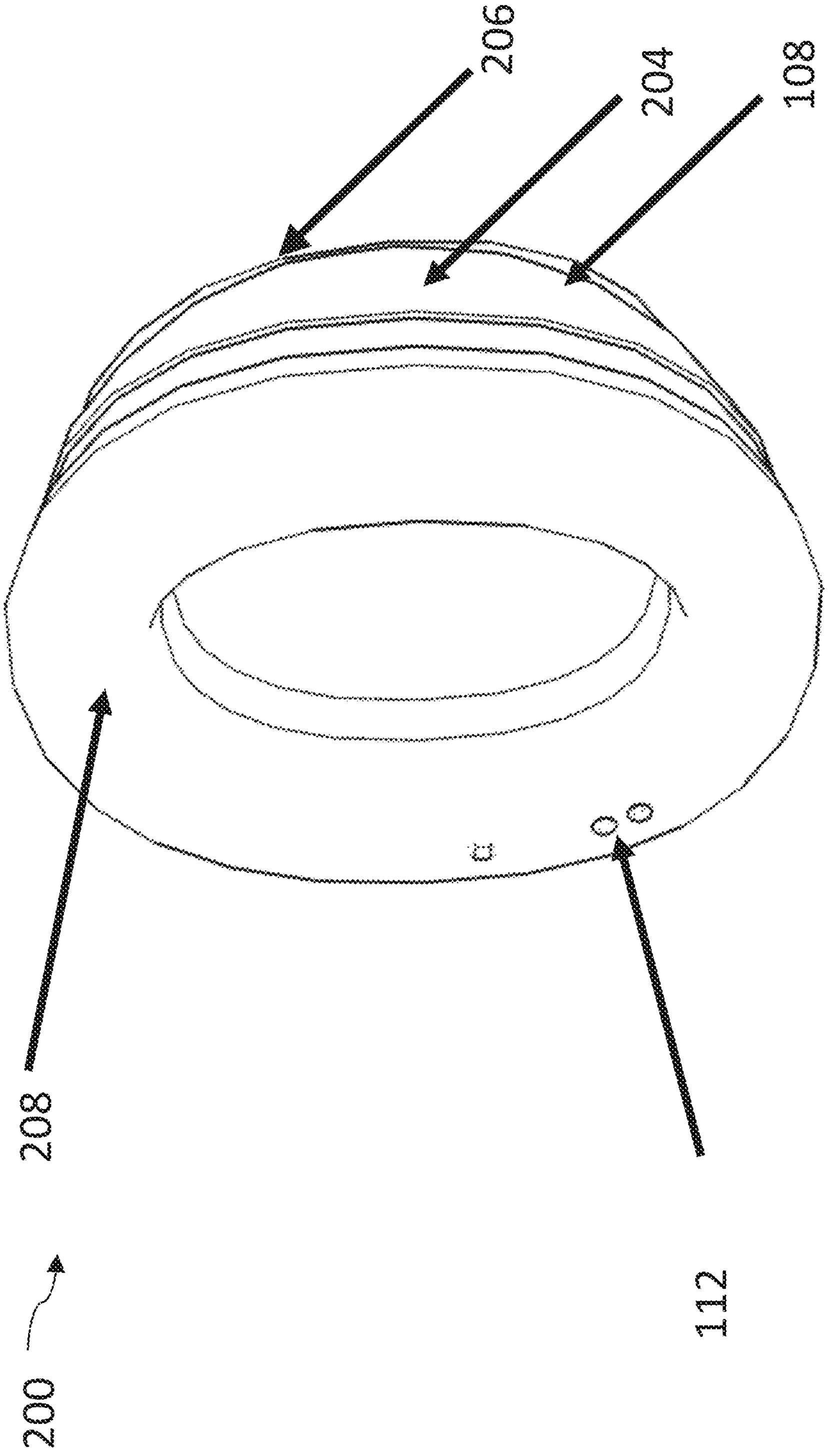
FIG. 2A is an exemplary embodiment of a perspective view of a headgear with physiological parameter measurement capabilities.
Figure 2B:
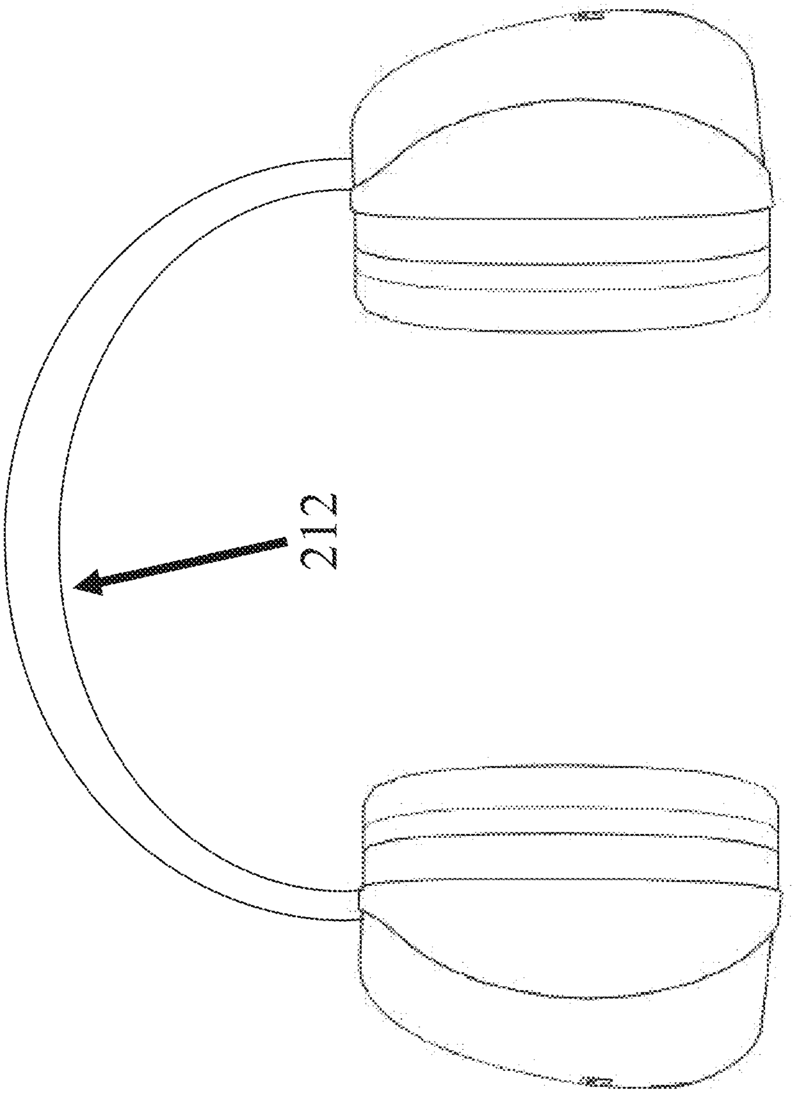
FIG. 2B is an exemplary embodiment of a Front view of a headgear with physiological parameter measurement capabilities.
Figure 2C:
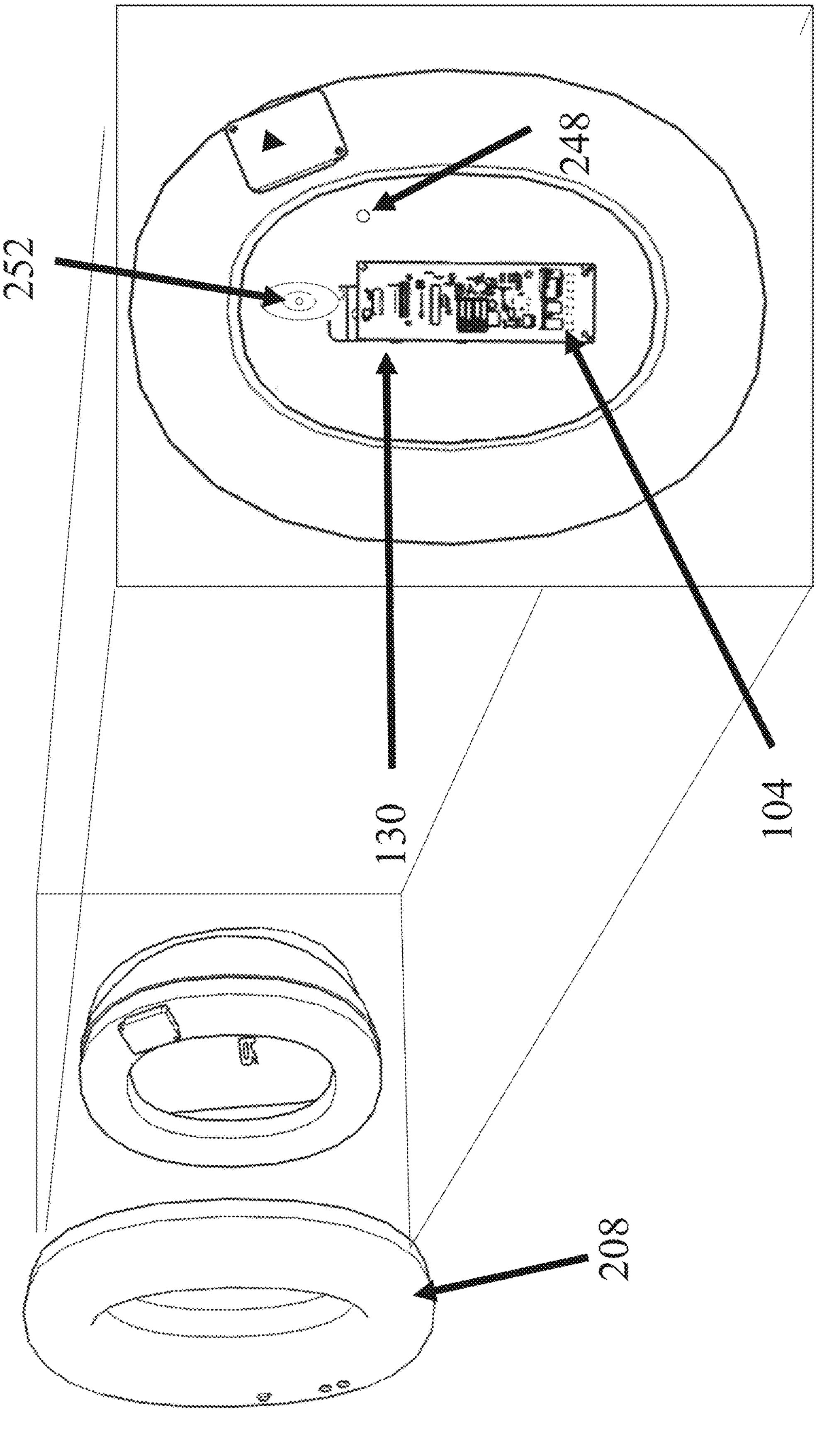
FIG. 2C is an exemplary embodiment of a perspective view of a headgear with physiological parameter measurement capabilities.

Referring now to FIGS. 2A-C, an exemplary embodiment of a perspective view of a headset with physiological parameter measurement capabilities is illustrated in FIG. 2A. An exemplary embodiment of a Front view of a headset with physiological parameters measurement capabilities is illustrated in FIG. 2B. An exemplary embodiment of a perspective view of a headset with physiological parameters measurement capabilities is illustrated in FIG. 2C.

Still referring to FIGS. 2A-C, at least a sensor 112 may be attached to a housing 204. In an embodiment, attachment to housing may include mounting on an exterior surface of housing or seal. In some embodiments at least a sensor 112 may be incorporated within housing 204. At least a sensor 112 may additionally be electrically connected to another element within housing 204, or the like. Alternatively or additionally, at least a sensor 112 may include a sensor that is not attached to housing 204 or is indirectly attached via wiring or the like. As a non-limiting example, at least a sensor 112 and/or one or more components thereof may be coupled to the substantially pliable seal 208. In an embodiment, at least a sensor 112 may be contacting exterior body surface; this may include direct contact with the exterior body surface, or indirect contact for instance through a portion of seal 208 or other components of headgear 100. As a non-limiting example of placement of at least a sensor 112, and as illustrated for exemplary purposes in FIGS. 2, at least a sensor 112 may include a sensor mounted on an edge of an earcup, and so positioned that placement of earcup over user's ear places sensor in contact with user's skin just behind the ear at a local skeletal eminence. Similarly, where housing 204 includes a mask as described above, a sensor of at least a sensor 112 may be disposed within mask at a location that, when mask is worn, places sensor against a forehead of user.

Still referring to FIG. 2A, Housing 204 may include a rigid outer shell.206. Rigid outer shell 206 may, for instance, protect internal elements of headset 200 from damage, and maintain them in a correct position on a user's body. Housing 204 and/or rigid outer shell 206 may be inserted on a head of the user, in particular the housing 204 may cover the ears of the user. As a non-limiting example, exterior body surface may be a surface, such as a surface of the head, face, or neck of user, which is wholly or partially covered by helmet, as described for example in further detail below. As a further non-limiting example, housing 204 may be formed to have a similar or identical shape to a standard-issue "ear cup" incorporated in an aviation helmet, so that housing 204 can replace ear cup after ear cup has been removed. Headset 200 may be the same or substantially the same as headgear 100.

Still referring to FIG. 2A, Seal 208 may be substantially pliable; seal 208 may be constructed of elastomeric, elastic, or flexible materials including without limitation flexible, elastomeric, or elastic rubber, plastic, silicone including medical grade silicone, gel, and the like. Substantially pliable seal 208 may include any combination of materials demonstrating flexible, elastomeric, or elastic properties, including without limitation foams covered with flexible membranes or sheets of polymer, leather, or textile material. As a non-limiting example, substantially pliable seal 208 may include any suitable pliable material for placement over a user's ear, including without limitation any pliable material or combination of materials suitable for use on headphones, headsets, earbuds, or the like. In an embodiment, substantially pliable seal 208 advantageously aids in maintaining housing 204 and/or other components of headset 200 against exterior body surface; for instance, where exterior body surface has elastomeric properties and may be expected to flex, stretch, or otherwise alter its shape or position to during operation, substantially pliable seal 208 may also stretch, flex, or otherwise alter its shape similarly under similar conditions, which may have the effect of maintaining seal 208 and/or one or more components of headgear 100 as described in greater detail below. Seal 208 may be attached to housing 204 by any suitable means, including without limitation adhesion, fastening by stitching, stapling, or other penetrative means, snapping together or otherwise engaging interlocking parts, or the like. Seal 208 may be removably attached to housing 204, where removable attachment signifies attachment according to a process that permits repeated attachment and detachment without noticeable damage to housing 204 and/or seal 208, and without noticeable impairment of an ability to reattach again by the same process. As a non-limiting example, substantially pliable seal 208 may be placed on an ear cup of the housing 204.

With continued reference to FIGS. 2B, housing 204 may be incorporated into a headset. A headset may include, without limitation, an aviation headset, such as headsets as manufactured by the David Clark company of Worcester Massachusetts, or similar apparatuses. A headset may also be used commercially for recreational use or fitness use. In some embodiments, housing 204 is headset; that is, wearable headgear may be manufactured by incorporating one or more components into the headset, using the headset as a housing 204. As a further non-limiting example, housing 204 may include a mask; a mask as used herein may include any device or element of clothing that is worn on a face of user during operation, occluding at least a part of the face. Masks may include, without limitation, safety googles, gas masks, dust masks, self-contained breathing apparatuses (SCBA), self-contained underwater breathing apparatuses (SCUBA), and/or other devices worn on and at least partially occluding the face for safety, functional, or aesthetic purposes. Wearable headgear may include a mask. Wearable headgear 200 may be manufactured by incorporating one or more elements or components of a mask in or on headset 200.

With continued reference to FIGS. 2B, a plurality of Housings 204 may attach to an element of headgear 212. As used in the current disclosure, a "headgear" is any element worn on and partially occluding a head or cranium of user. In an embodiment, a headgear 212 may attach two housings 204 in a manner which they may be worn around the head. Headgear 212 may wholly or partially occlude user's face and thus also include a mask; headgear 212 may include, for instance, a fully enclosed diving helmet, space helmet, or helmet incorporated in a space suit, or the like. Headgear 212 may include a headband, such as without limitation a headband of a headset. As used in the current disclosure, a "headband" is a band in a horseshoe shape configured to be worn over the top of the head of the user. Additionally, the headband may be connecting piece that runs from a first housing 204 to a second housing 204. The headband may hold them together so that you can comfortably and securely wear the headset 200 on your head. In an embodiment, the housing 204 may be electrically connected by running a wire through the headband. Headgear 212 may include a hat, a helmet, a construction "hardhat," a bicycle helmet, or the like.

With continued reference to FIG. 2C, housing 204 may house a plurality of hardware associated with wearable headgear 100 including, but not limited to, processor 104, microphone 248, speaker 252, environmental sensor 130. Housing 204 may be configured mounted to an exterior body surface of a user; exterior body surface may include, without limitation, skin, hair, an interior surface of an orifice such as the mouth, nose, or ears, or the like. Exterior body surface and/or locus may include an exterior body surface of user's head, face, or neck. Environmental temperature sensor 130 may be positioned to within earcup to measure temperature of ambient air proximal skin surface, thereby providing a relative temperature measurement for skin temperature.

With continued reference to FIG. 2C, in an embodiment, at least a sensor 112 may contact a locus on the exterior body surface where substantially no muscle is located between the exterior body surface and an underlying bone structure, meaning muscle is not located between the exterior body surface and an underlying bone structure and/or any muscle tissue located there is unnoticeable to a user as a muscle and/or incapable of appreciably flexing or changing its width in response to neural signals; such a locus may include, as a non-limiting example, locations on the upper cranium, forehead, nose, behind the ear, at the end of an elbow, on a kneecap, at the coccyx, or the like. Location at a locus where muscle is not located between exterior body surface and underlying bone structure may decrease reading interference and/or inaccuracies created by movement and flexing of muscular tissue. At least a sensor 112 may contact a locus having little or no hair on top of skin. At least a sensor 112 may contact a locus near to a blood vessel, such as a locus where a large artery such as the carotid artery or a branch thereof, or a large vein such as the jugular vein, runs near to skin or bone at the location; in an embodiment, such a position may permit at least a sensor 116, 144 to detect circulatory parameters as described above.

Figure 3:
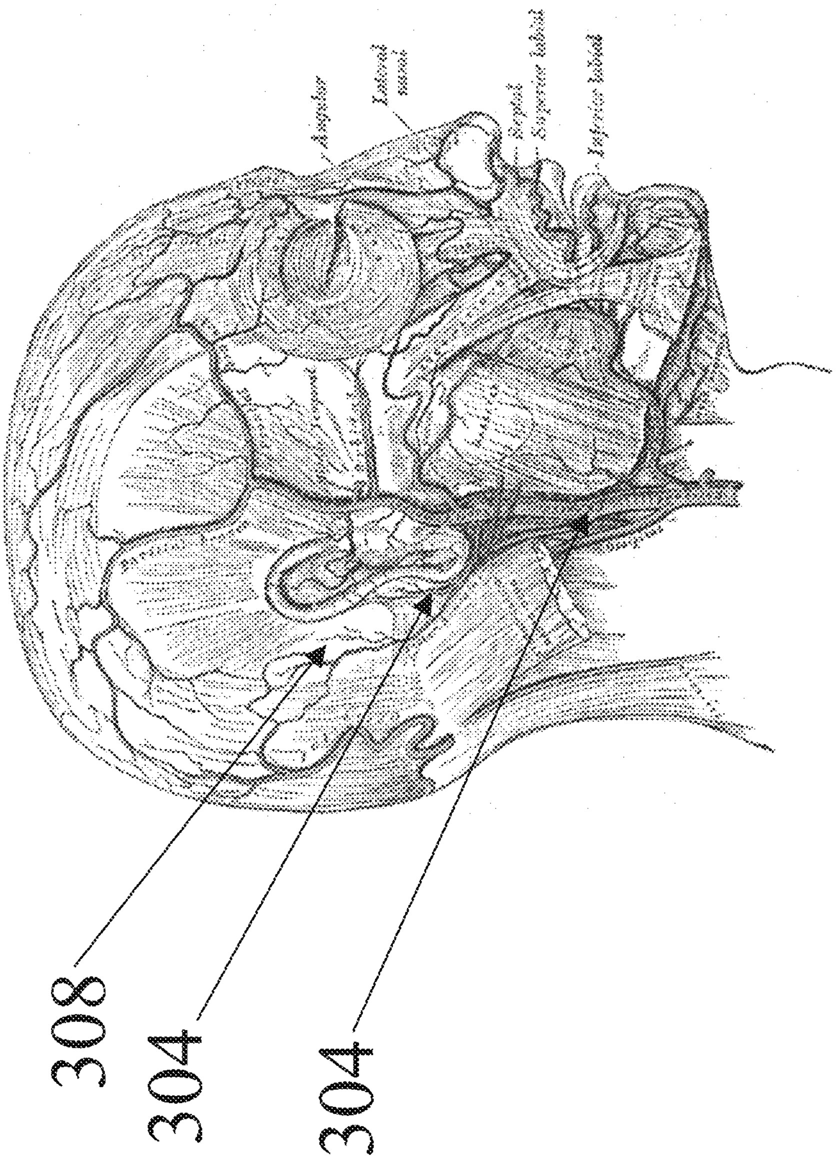
FIG. 3 is a schematic diagram of some aspects of user cranial anatomy in an embodiment.

Referring now to FIG. 3, a schematic diagram of anatomy of a portion of a user cranium 300 is illustrated for exemplary purposes. At least a sensor 112 may, for instance, be placed at or near to a locus adjacent to a branch 304 of a carotid artery, which may be a branch of an exterior carotid artery. At least a sensor 112 may be placed at a location 308 where substantially no muscle is found between a user's skin and bone; such a location may be found, for instance, near to the user's neck behind the ear. In an embodiment, at least a physiological sensor may be placed in a locus that is both adjacent to a branch 304 of a carotid artery and has substantially no muscle between skin and bone. In an embodiment, measurement of at least a physiological parameter, including without limitation pulse oxygenation and/or pulse rate as described in further detail below, on a particular portion of the cranium may eliminate interfering factors such as sweat and movement artifact; measurement above the neck may further eliminate measurement issues experienced at the extremities (finger, wrist) due to temperature variation, movement and blood pooling under G. Where at least a sensor 112 is used, at least two sensors may be placed at two locations on a user's cranium; for instance, two sensors, one on each side of the cranium, may provide validation of consistent data, and assures a high capture rate of data in flight. Two sensors may be so placed, as noted elsewhere in this disclosure, by form and/or configuration of housing; for instance, housing may include two earcups or other over-ear devices as described above.

Figure 4:
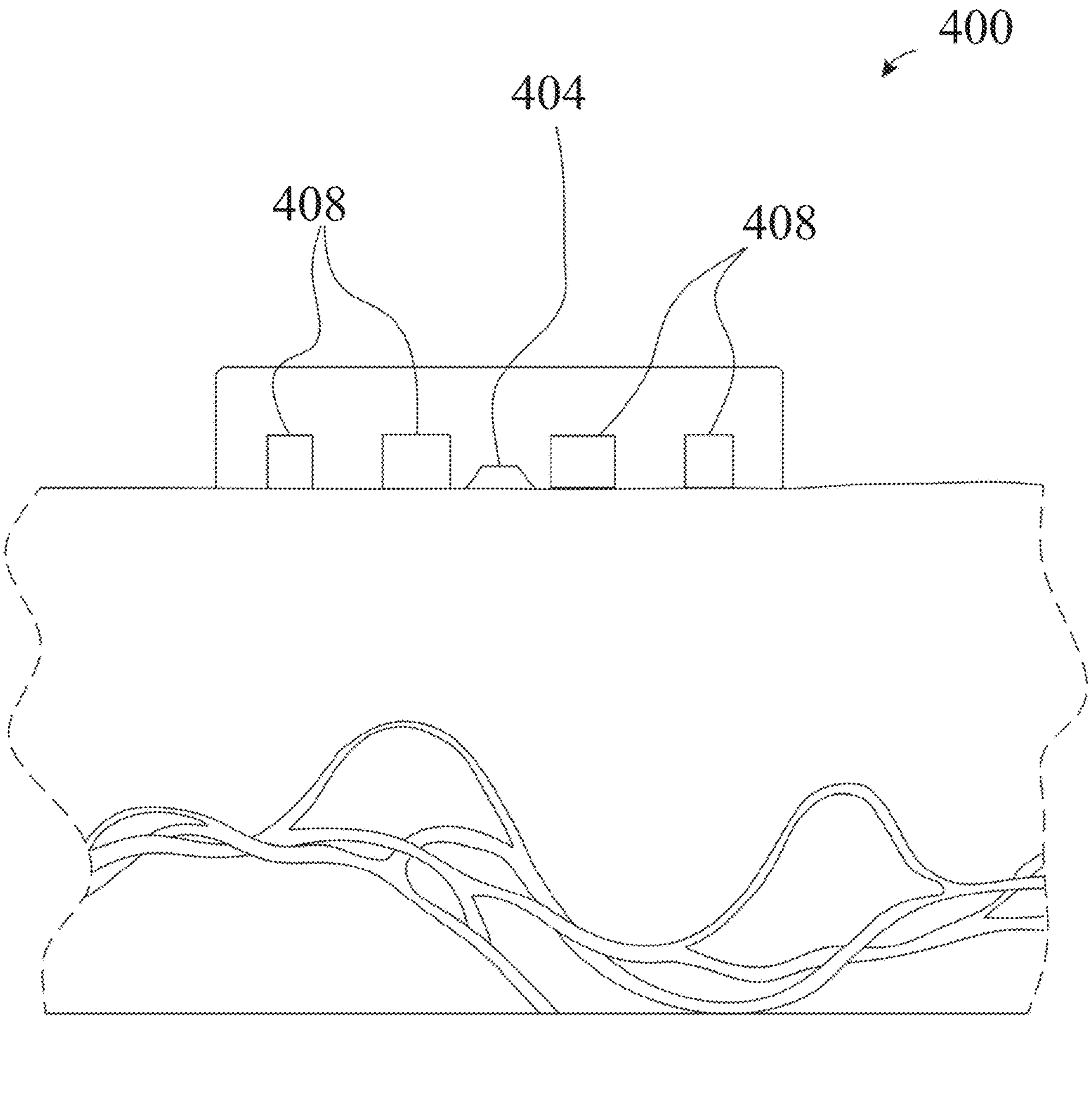
FIG. 4 is a schematic illustration of an exemplary embodiment of a near-infrared spectroscopy sensor.

Now referring to FIG. 4, an exemplary embodiment of a NIRS 400 against an exterior body surface, which may include skin, is illustrated. NIRS 400 may include a light source 404, which may include one or more light-emitting diodes (LEDs) or similar element. Light source 404 may, as a non-limiting example, convert electric energy into near-infrared electromagnetic signals. Light source 404 may include one or more lasers. NIRS 400 may include one or more detectors 408 configured to detect light in the near-infrared spectrum. Although the wavelengths described herein are infrared and near-infrared, light source 404 may alternatively or additionally emit light in one or more other wavelengths, including without limitation blue, green, ultraviolet, or other light, which may be used to sense additional physiological parameters. In an embodiment, light source may include one or more multi-wavelength light emitters, such as one or more multi-wavelength LEDs, permitting detection of blood-gas toxicology. Additional gases or other blood parameters so detected may include, without limitation CO4 saturation levels, state of hemoglobin as opposed to blood oxygen saturation generally. One or more detectors 408 may include, without limitation, charge-coupled devices (CCDs) biased for photon detection, indium gallium arsenide (InGaAs) photodetectors, lead sulfide (PbS) photodetectors, or the like. NIRS 400 may further include one or more intermediary optical elements (not shown), which may include dispersive elements such as prisms or diffraction gratings, or the like. In an embodiment, NIRS 400 may be used to detect one or more circulatory parameters, which may include any detectable parameter further comprises at least a circulatory parameter. At least a sensor 112 may include at least two sensors mounted on opposite sides of user's cranium.

Figure 5:
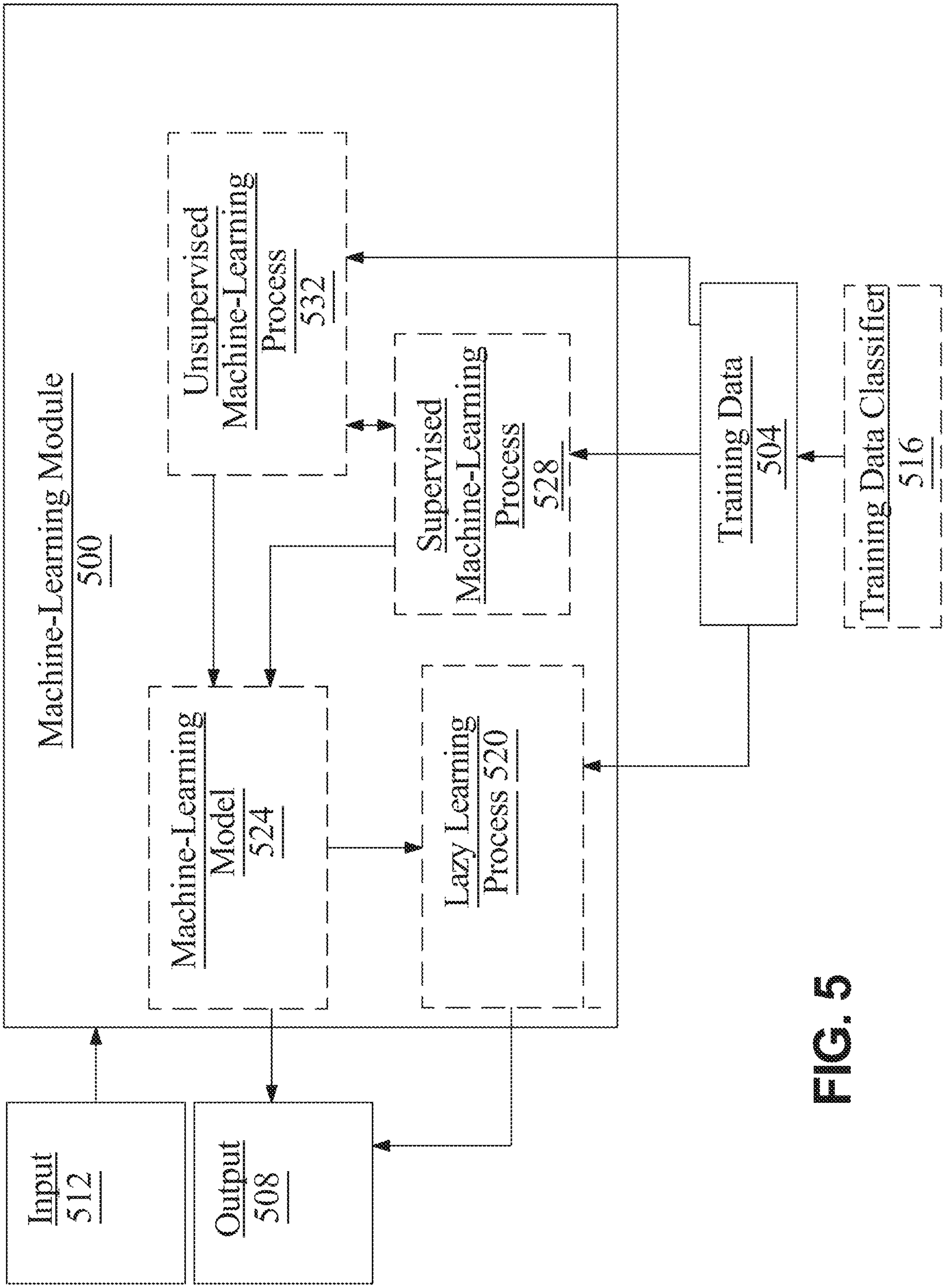
FIG. 5 is a block diagram of an exemplary machine-learning process

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm instantiated in hardware or software logic, data structures, and/or functions that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example, at least a signal as inputs correlated a detected reaction as outputs.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to elements of action responses.

With further reference to FIG. 5, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 5, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may identified as having poor quality data, where "poor quality" is defined as having a signal to noise ratio below a threshold value.

As a non-limiting example, and with further reference to FIG. 5, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 5, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units In some embodiments, and with continued reference to FIG. 5, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naive Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include at least a signal as described above as inputs, action responses as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

With further reference to FIG. 5, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 5, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 532 may not require a response variable; unsupervised processes 532 may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 5, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 5, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 5, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 5, one or more processes or algorithms described above may be performed by at least a dedicated hardware unit 536. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 536 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 536 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 536 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 6:
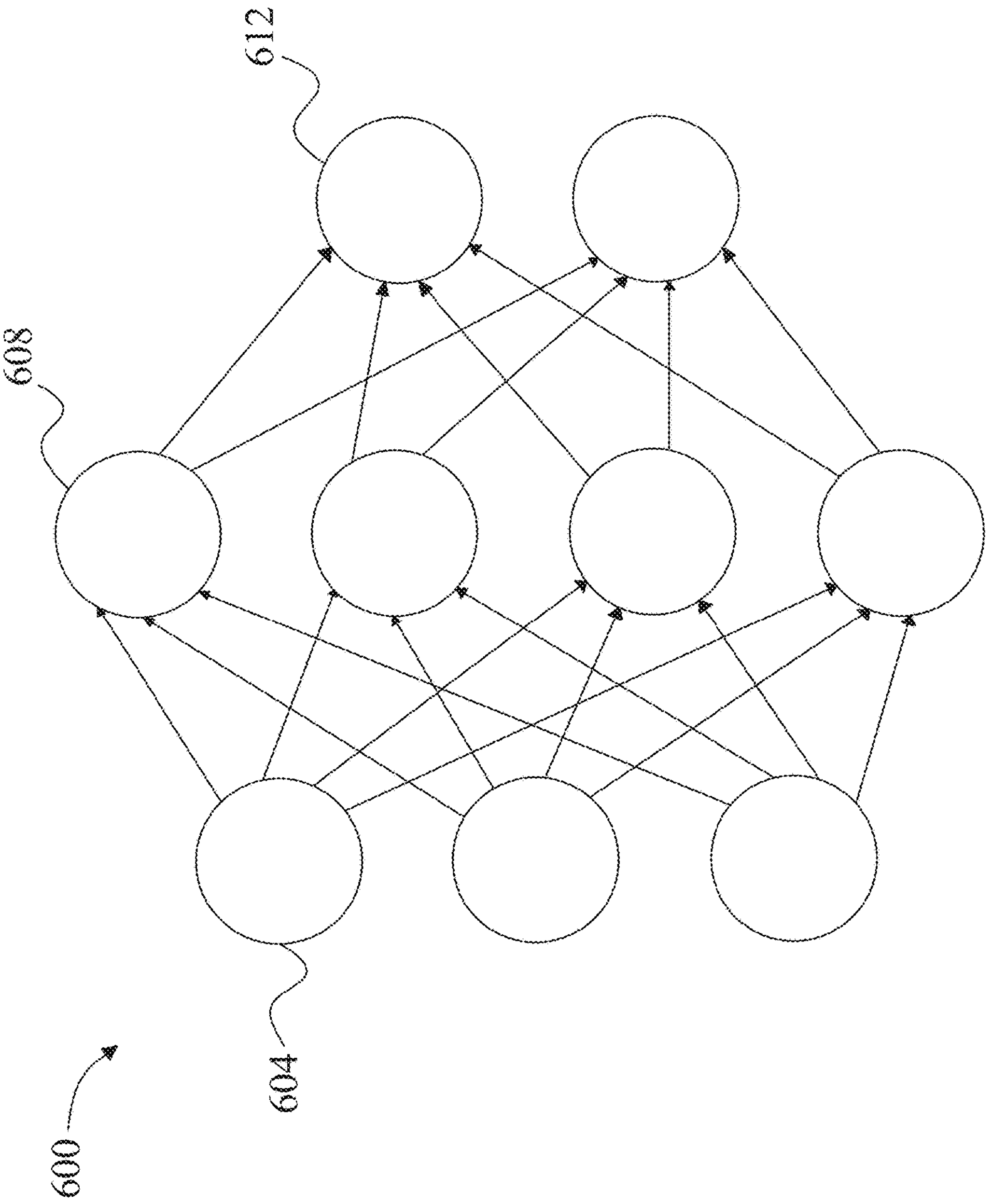
FIG. 6 is a diagram of an exemplary embodiment of a neural network.

Referring now to FIG. 6, an exemplary embodiment of neural network 600 is illustrated. A neural network 600 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 606, one or more intermediate layers 608, and an output layer of nodes 612. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 7:
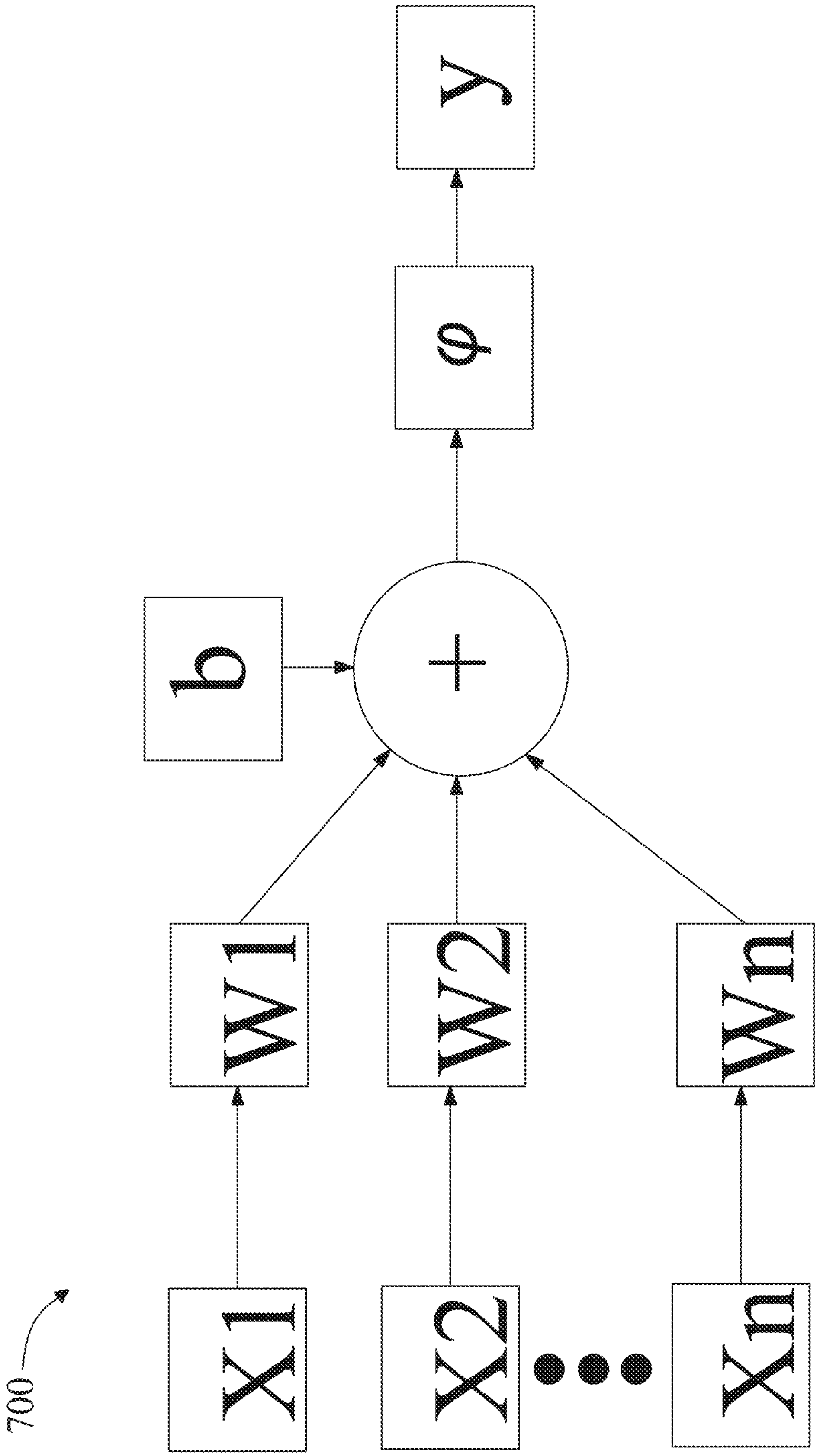
FIG. 7 is a diagram of an exemplary embodiment of a node of a neural network.

Referring now to FIG. 7, an exemplary embodiment of a node of a neural network is illustrated. A node may include, without limitation, a plurality of inputs xi that may receive numerical values from inputs to a neural network containing the node and/or from other nodes. Node may perform a weighted sum of inputs using weights $w_i$ that are multiplied by respective inputs xi. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input xi may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 8:
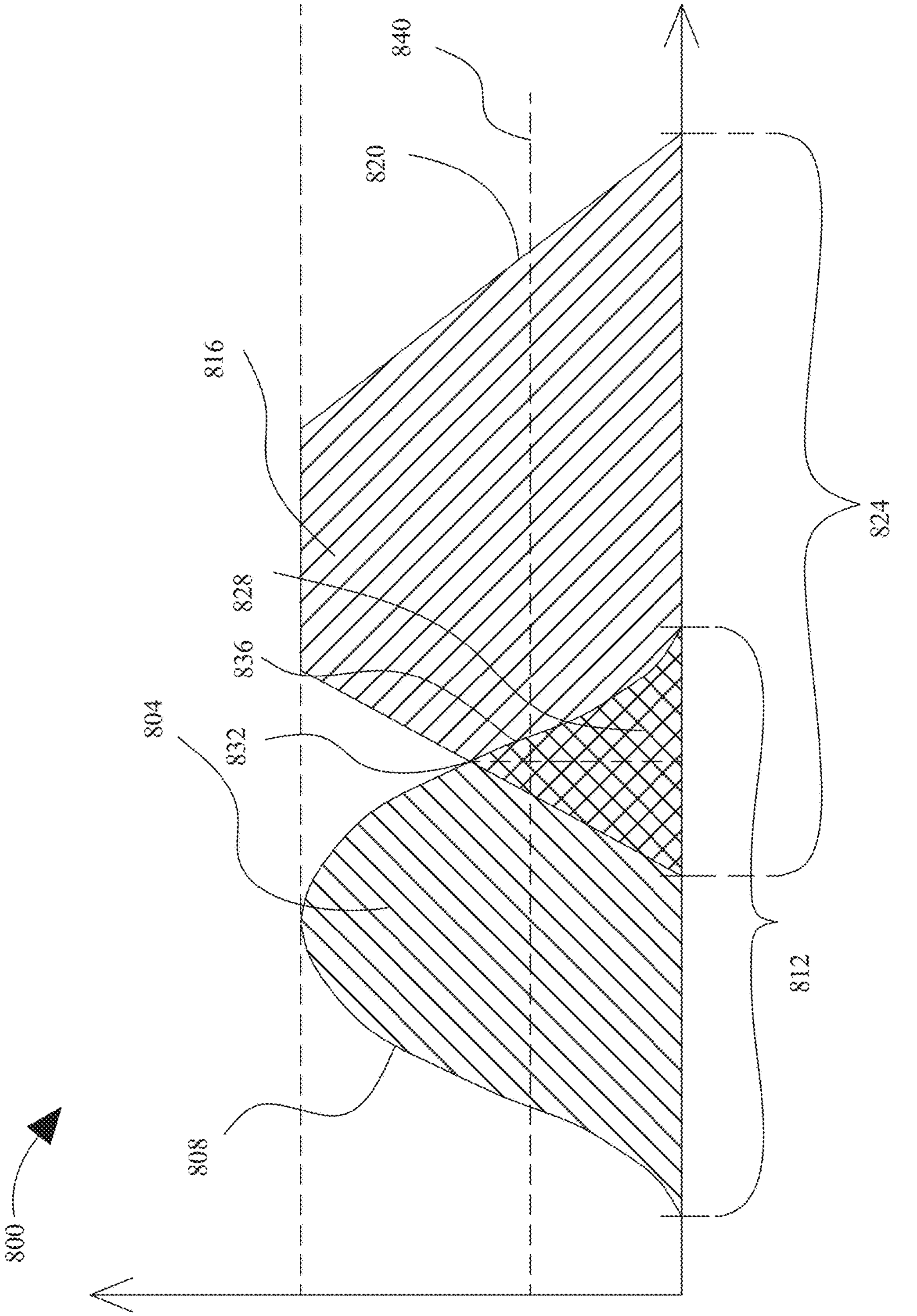
FIG. 8 is an illustration of an exemplary embodiment of fuzzy set comparison.

Now referring to FIG. 8, an exemplary embodiment of fuzzy set comparison 800 is illustrated. In a non-limiting embodiment, the fuzzy set comparison. In a non-limiting embodiment, fuzzy set comparison 800 may be consistent with fuzzy set comparison in FIG. 1. In another non-limiting the fuzzy set comparison 800 may be consistent with the name/version matching as described herein. For example and without limitation, the parameters, weights, and/or coefficients of the membership functions may be tuned using any machine-learning methods for the name/version matching as described herein. In another non-limiting embodiment, the fuzzy set may represent sensor outputs and action responses from FIG. 1.

Alternatively or additionally, and still referring to FIG. 8, fuzzy set comparison 600 may be generated as a function of determining the data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 8, inference engine may be implemented according to input plurality of sensor output data. For instance, an acceptance variable may represent a first measurable value pertaining to the classification of contextual data to inquiry response data. Continuing the example, an output variable may represent diagnostic data associated with the user. In an embodiment, plurality of sensor output data may be represented by their own fuzzy set. In other embodiments, the classification of the data into diagnostic data may be represented as a function of the intersection two fuzzy sets as shown in FIG. 8, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T (T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

A first fuzzy set 804 may be represented, without limitation, according to a first membership function 808 representing a probability that an input falling on a first range of values 812 is a member of the first fuzzy set 804, where the first membership function 808 has values on a range of probabilities such as without limitation the interval [0,1], and an area beneath the first membership function 808 may represent a set of values within first fuzzy set 804. Although first range of values 812 is illustrated for clarity in this exemplary depiction as a range on a single number line or axis, first range of values 812 may be defined on two or more dimensions, representing, for instance, a Cartesian product between a plurality of ranges, curves, axes, spaces, dimensions, or the like. First membership function 808 may include any suitable function mapping first range 812 to a probability interval, including without limitation a triangular function defined by two linear elements such as line segments or planes that intersect at or below the top of the probability interval. As a non-limiting example, triangular membership function may be defined as:

$$(x, a, b, c) = \begin{cases} 0, \text{ for } x > c \text{ and } x < a \\ \frac{x-a}{b-a}, \text{ for } a \le x < b \\ \frac{c-x}{c-b}, \text{ if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 804 may represent any value or combination of values as described above, including any sensor output and action response data. A second fuzzy set 816, which may represent any value which may be represented by first fuzzy set 804, may be defined by a second membership function 820 on a second range 824; second range 824 may be identical and/or overlap with first range 812 and/or may be combined with first range via Cartesian product or the like to generate a mapping permitting evaluation overlap of first fuzzy set 804 and second fuzzy set 816. Where first fuzzy set 804 and second fuzzy set 816 have a region 838 that overlaps, first membership function 808 and second membership function 820 may intersect at a point 832 representing a probability, as defined on probability interval, of a match between first fuzzy set 804 and second fuzzy set 816. Alternatively or additionally, a single value of first and/or second fuzzy set may be located at a locus 838 on first range 812 and/or second range 824, where a probability of membership may be taken by evaluation of first membership function 808 and/or second membership function 820 at that range point. A probability at 828 and/or 832 may be compared to a threshold 840 to determine whether a positive match is indicated. Threshold 840 may, in a non-limiting example, represent a degree of match between first fuzzy set 804 and second fuzzy set 816, and/or single values therein with each other or with either set, which is sufficient for purposes of the matching process; for instance, the classification into one or more query categories may indicate a sufficient degree of overlap with fuzzy set representing at least a sensor 112 and inquiry response data for combination to occur as described above. Each threshold may be established by one or more user inputs. Alternatively or additionally, each threshold may be tuned by a machine-learning and/or statistical process, for instance and without limitation as described in further detail below.

In an embodiment, a degree of match between fuzzy sets may be used to rank one resource against another. For instance, if both at least a sensor 112 and inquiry response data have fuzzy sets, inquiry response data may be generated by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 9:
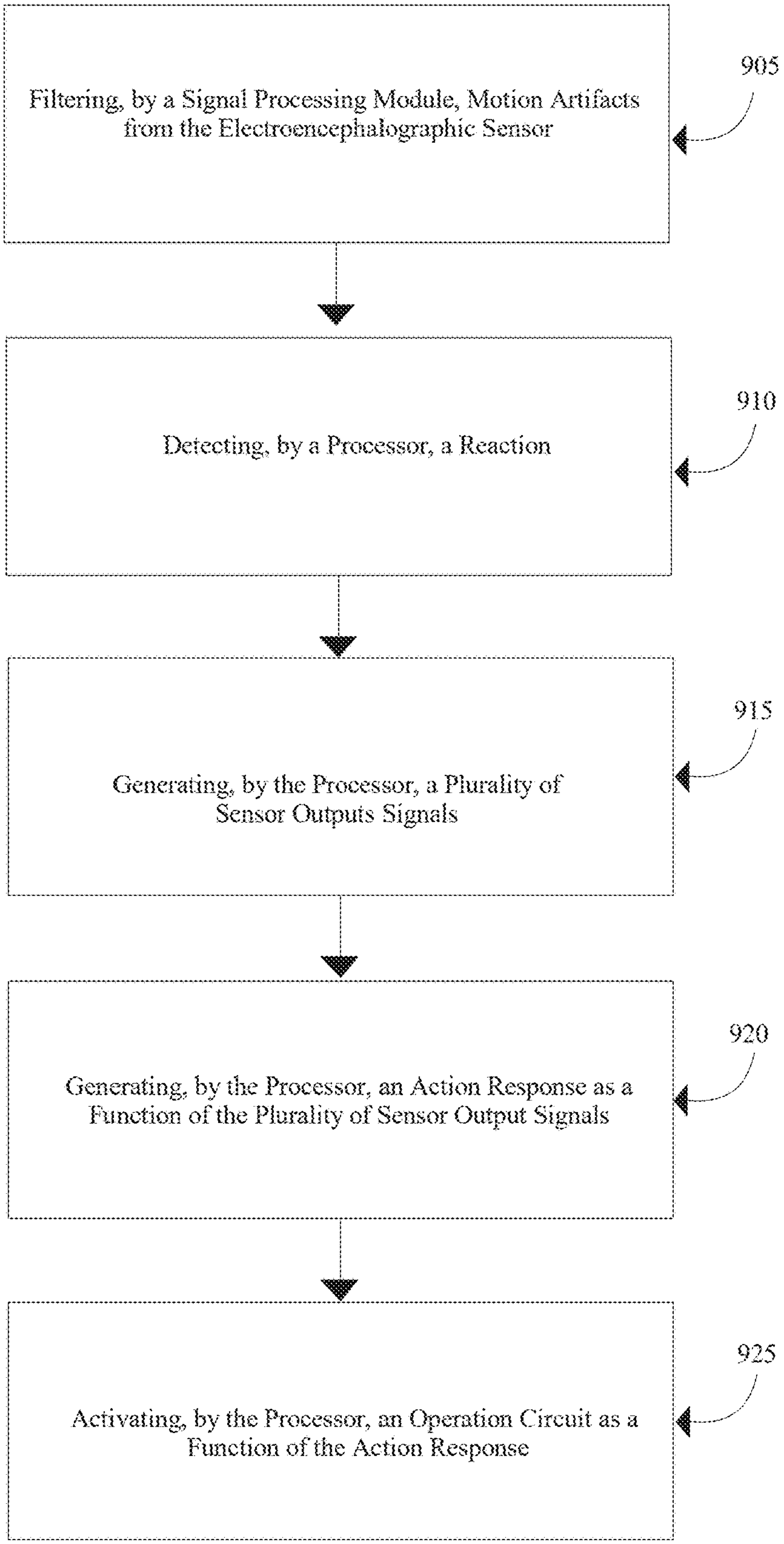
FIG. 9 is a flow diagram illustrating an exemplary method for manufacturing a wearable headgear.

Referring now to FIG. 9, an exemplary method of method 900 for manufacturing a wearable headgear is illustrated using a flow diagram. At step 905, method 900 may include filtering, by a signal processing module, motion artifacts from an electroencephalographic sensor. This may be implemented as described with reference to FIGS. 1-8. In an embodiment, detecting a reaction includes determining a cognitive state of a user. In an embodiment, filtering motion artifacts includes training an adaptive filter in a signal processing unit.

With continued reference to FIG. 9 at step 910, method 900 may include detecting, by the processor, a reaction. This may be implemented as described with reference to FIGS. 1-8. In an embodiment, detecting a reaction includes determining a cognitive state of a user.

With continued reference to FIG. 9, step 915 of method 900 may include generating a plurality of sensor output signals indicating a detected reaction. This may be implemented as described with reference to FIGS. 1-8.

With continued reference to FIG. 9, step 920 of method 900 may include generating an action response as a function of the plurality of sensor output signal. This may be implemented with reference to FIGS. 1-8. In an embodiment, the action response includes a filtration process. In another embodiment, the action response includes generating an action response machine learning model.

With continued reference to FIG. 9, step 925 of method 900 may include activating an operation circuit as a function of the action response. This may be implemented with reference to FIGS. 1-8. In another embodiment, the action response includes at least an interaction with the user.

Figure 10:
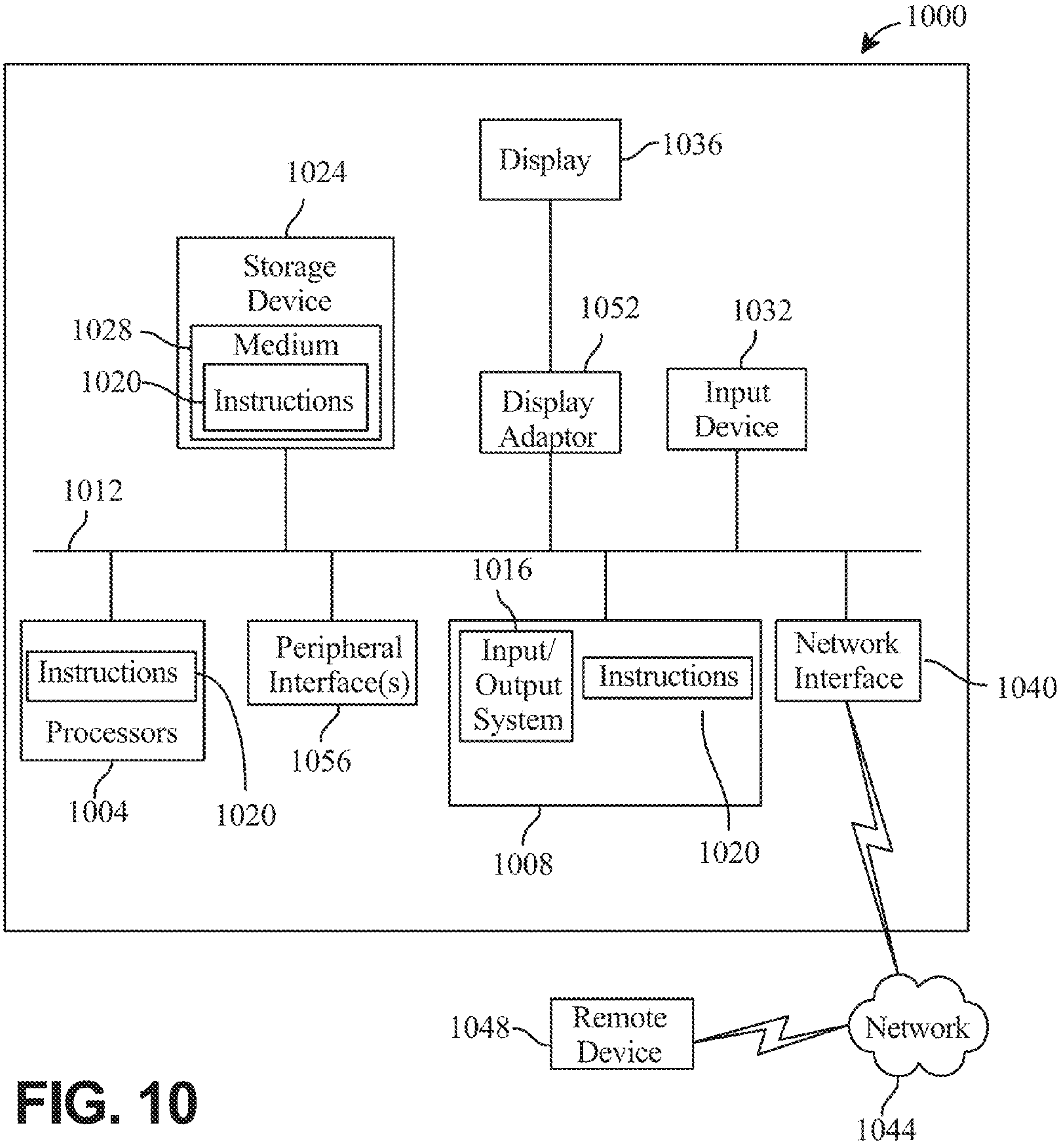
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A wearable headgear comprising:

a housing configured to be placed on a head of a user, wherein the housing comprises an earcup containing a pliable seal;

a plurality of sensors positioned within the housing, wherein:

the plurality of sensors comprise:

at least an electroencephalographic sensor; and at least a circulatory sensor;

a signal processing module communicatively connected to the at least an electroencephalographic sensor, wherein the signal processing module is configured to filter motion artifacts from the electroencephalographic sensor by utilizing an adaptive filter to inspect a signal of the electroencephalographic sensor over time and identify segments that are likely to be contaminated with motion artifacts;

a software protocol operating on at least a processor, the software protocol configured to minimize the motion artifacts by directing a placement of the wearable headgear to the user based on the motion artifacts;

the at least a processor; and a memory communicatively connected to the at least a processor, the memory containing instructions configuring the at least a processor to:

receive, from the plurality of sensors, one or more electrical signals;

detect a reaction associated with the user by comparing the one or more electrical signals to a threshold level;

generate a plurality of sensor output signals as a function of the reaction;

generate an action response as a function of the plurality of sensor output signals; and activate an operation circuit as a function of the action response.

2. The wearable headgear of claim 1, wherein detecting the reaction comprises determining a cognitive state of the user.

3. The wearable headgear of claim 1, wherein at least one sensor from the plurality of sensors measures at least an oxygenation signal.

4. The wearable headgear of claim 1, wherein the action response comprises a filtration process.

5. The wearable headgear of claim 1, wherein the plurality of sensors further comprise an optical sensor.

6. The wearable headgear of claim 5, wherein the optical sensor is configured to employ optical tracking.

7. The wearable headgear of claim 1, wherein generating the action response comprises generating an action response machine learning model, wherein generating the action response machine learning model comprises:

training the action response machine learning model using action response training data, wherein the action response training data comprises inputs correlated to outputs; and updating the action response machine learning model as a function of the outputs.

8. The wearable headgear of claim 1, wherein activating the operation circuit comprises at least an interaction with the user.

9. The wearable headgear of claim 1, wherein directing the placement of the wearable headgear comprises providing directional guidance instructing the user to adjust a sensor position of at least one sensor of the plurality of sensors through one or more voice prompts.

* * * * *